(12) United States Patent
Hudson et al.

(10) Patent No.: US 6,503,543 B1
(45) Date of Patent: Jan. 7, 2003

(54) TRYPTOPHAN SOURCE FROM PLANTS AND USES THEREFOR

(76) Inventors: Craig J. Hudson, 253 Cambria Street, Stratford, Ontario (CA), N5A 1H9; Susan P. Hudson, 253 Cambria Street, Stratford, Ontario (CA), N5A 1H9

( * ) Notice: Subject to any disclaimer, the term of this patent is extended or adjusted under 35 U.S.C. 154(b) by 0 days.

(21) Appl. No.: 09/580,914

(22) Filed: May 26, 2000

(51) Int. Cl.$^7$ .......................... A61K 35/78; A01N 43/04
(52) U.S. Cl. .......................... 424/758; 514/23; 514/419
(58) Field of Search .......................... 800/250; 514/923, 514/816, 23, 419; 435/108; 424/725, 195.17, 750, 757, 758, 768, 776

(56) References Cited

U.S. PATENT DOCUMENTS

| | | | |
|---|---|---|---|
| 2,638,433 A | | 5/1953 | George |
| 3,930,055 A | | 12/1975 | Engelman et al. |
| 4,054,665 A | | 10/1977 | Eberle et al. |
| 4,307,118 A | * | 12/1981 | Kajs |
| 4,421,746 A | * | 12/1983 | Kojima et al. |
| 4,551,335 A | * | 11/1985 | Canella et al. |
| 4,897,380 A | | 1/1990 | Pollack et al. |
| 5,002,780 A | | 3/1991 | Bakta et al. |
| 5,277,910 A | * | 1/1994 | Hidvegi |
| 5,470,846 A | * | 11/1995 | Sandyk |
| 5,567,424 A | | 10/1996 | Hastings |
| 5,612,074 A | * | 3/1997 | Leach |
| 5,738,887 A | * | 4/1998 | Wu |
| 5,882,672 A | * | 3/1999 | Kojima et al. |
| 5,885,976 A | | 3/1999 | Sandyk |
| 5,919,511 A | * | 7/1999 | Hagiwara et al. |
| 5,968,519 A | | 10/1999 | Youssefyeh et al. |
| 6,294,520 B1 | * | 9/2001 | Naito |

FOREIGN PATENT DOCUMENTS

| | | |
|---|---|---|
| EP | 0 147 688 | 7/1985 |
| EP | 0652012 * | 5/1995 |
| FR | 1485766 | 6/1967 |
| FR | 2 777 751 | 10/1999 |
| GB | 388319 | 2/1933 |
| WO | WO 95/19716 * | 11/1995 |
| WO | WO 99/61038 | 5/1999 |

OTHER PUBLICATIONS

Oyenuga et al., J. Sci. Fd. Argic. 1975, 26: 843–854. Some aspects of the biochemistry and nutritive value of the water melon seed (Citrullus vulgaris, Schrad).*

Edwards et al., J. of Nutrition, 1946. 32(6): 597–611. Biological value of proteins in relation to the essential amino acids which they contain.*

Eagles, "The British Journal of Psychiatry," *Royal Medico-Psychological Association*, 157:937–938 (1990).

Allegri et al, Food Chemistry, vol. 47, No. 1, pp. 23–27 (1993).

* cited by examiner

*Primary Examiner*—Christopher R. Tate
*Assistant Examiner*—Michele C. Flood
(74) *Attorney, Agent, or Firm*—Morgan, Lewis & Bockius LLP

(57) ABSTRACT

Compositions are described comprising at least partially defatted meal from a plant source naturally containing tryptophan, preferably squash seeds, and a carbohydrate source provided in an amount capable of facilitating transport of the tryptophan across the blood brain barrier. Also described are dietary supplements, foods and beverages comprising the composition of the invention to induce sleep or provide tryptophan supplementation to individuals in need thereof.

14 Claims, No Drawings

TRYPTOPHAN SOURCE FROM PLANTS AND USES THEREFOR

BACKGROUND OF THE INVENTION

Tryptophan is a naturally occurring essential amino acid that has a number of interesting medicinal qualities including treatment of insomnia as well as an adjunct in the treatment of a number of psychiatric disorders. After absorption, tryptophan circulates in the blood (approximately 80% bound to plasma albumin with the remaining 20% circulating as free tryptophan) and under appropriate conditions tryptophan is transported into the brain. Once across the blood brain (BBB), tryptophan becomes available for metabolism into serotonin, a neurotransmitter implicated in mood and sleep regulation (Boman, 1988). Serotonin, in turn, is metabolized to melatonin; a sleep related hormone found in the pineal gland, a small cone-like structure in the epithalamus of the brain that regulates the 24-hour circadian rhythm in humans. Ingestion of a sufficient quantity of tryptophan consistently results in reduced sleep latency (the time from "lights out" to sleep) and an improvement in overall quality of sleep through improved sleep architecture (Boman, 1988). Tryptophan metabolism to serotonin also serves well in conditions where depleted serotonin levels exists such as anxiety disorders, depression, obsessive-compulsive some pain disorders, aggression and eating disorders.

SUMMARY OF THE INVENTION

A naturally derived, tryptophan-rich composition with several unique characteristics has been developed by enriching the tryptophan content of a tryptophan-rich protein source. Compositions of the invention comprise a plant source naturally containing tryptophan, preferably squash seeds, such as butternut squash seeds, peppercorn squash seeds and pumpkin seeds. Preferably, the plant source is at least partially defatted to concentrate the tryptophan content. The composition further comprises a carbohydrate sources such as glucose, in an amount sufficient to facilitate uptake of tryptophan across the blood brain barrier and to circumvent the competition for BBB transport sites into the central nervous system (CNS). The composition can optionally comprise physiologically acceptable vehicle(s), flavorings, colors and other nutrients, such as vitamins, preferably vitamin B3 and/or vitamin B6.

In a preferred embodiment, the composition comprises at least partially defatted squash seeds, particularly butternut squash, pumpkin and peppercorn squash seeds, glucose and vitamins B3 and B6.

The invention further pertains to dietary supplements (e.g., tablet, powder, suspension, liquid, capsule or gel), foods (e.g., dietary bar, cookie, baked good, snack food, candy, candy bars) and beverages comprising the composition of the invention.

The compositions of the invention can be used to induce sleep in an individual in need thereof, such as those suffering from insomnia or condition associated with a sleep disorder. Alternatively, the compositions can be administered to an individual to improve their tryptophan metabolism, such as for those individuals suffering from a condition or disease associated with reduced levels of serotonin. The compositions can be used as a hypnotic, but may also serve a role in clinical states associated with reduced levels of serotonin, a tryptophan metabolite: depression, anxiety states including obsessive-compulsive disorder, eating disorders and chronic pain.

DETAILED DESCRIPTION OF THE INVENTION

It has been discovered, using second derivative spectroscopy, that certain plant sources and specifically plant seeds possess high levels of naturally occurring tryptophan and that these materials can be used as natural sources of tryptophan. Based upon this discovery, a process has been developed to produce compositions having enhanced levels of tryptophan as a natural protein source of tryptophan richer than any known source. Plants that use gramine typically contain high levels of tryptophan and can be used herein as the plant. source. It is desirable, but not essential, that the starting plant material contain at least 200 mg/100 g or at least 0.2% tryptophan, Tryptophan concentration can be determined using known methods including high pressure liquid chromatography (HPLC), second derivative spectroscopy or any other known methodology. Second derivative spectroscopy is the preferred method to quantitatively analyze tryptophan levels as it eliminates background absorbence. See the Examples section.

According to an embodiment of the invention, tryptophan levels present in the plant source are enhanced using a series of steps to extract oil from the plant material, thus rendering the material partially defatted. The plant source can be a seed such as, but not limited to, butternut squash seed, peppercorn squash seed, pumpkin seed, lentil seed, sunflower seed, flax seed, watermelon seed, sisymbrium seed, cotton seed, sesame seed, canola seed, evening primrose seed, barley, safflower seed, alfalfa seed, soy beans and combinations thereof. Preferably, the seed is a butternut squash seed as it is believed to contain the highest ratio of tryptophan to total proteins, relative to other seed types. The plant source can also be a vegetative part of the plant, such as alfalfa, seaweed or kelp. Although it is preferred to partially defat the plant source to enhance tryptophan levels, defatting is not essential to practice the invention.

In the case of seeds, it is not necessary to remove their seed coat or hull to expose the endosperm prior to processing. The seed is first processed ("flaking") through a series of smooth rollers to produce a thin flake. This step allows the oil cells to at least partially rupture and increases the surface area of the seeds for further treatment.

The flaked seeds are then heat treated ("cooking or conditioning") to further rupture oil cells and increase the oil viscosity for subsequent defatting. The conditioning step can be performed using for example a microwave, an oven or by indirect steam. The temperature of the conditioning step should be sufficient to rupture the oil cells and increase the viscosity of the oil without detrimentally destroying proteins contained in the plant material. Preferably, the temperature will be from about 40° C. to about 50° C. The conditioning step is performed for a period of time sufficient to achieve the goal temperature.

Prior to cooling, the heated seed flakes are then mechanically pressed ("pressing") to at least partially remove the oil contained therein. Any known mechanical press or expeller can be used, such as a Gusta Lab Press. The degree of defatting will depend in part on the flaking and cooking steps performed, temperature and oil viscosity and the pressure exerted on the seed. Typically from about two thirds to about three quarters of the oil should be removed.

The pressed plant material can then be further processed depending upon the end user. For example, the plant material can be milled using any conventional means such as but not limited to a disk mill, hammer mill or pin mill. The type of mill selected will depend in part upon the consistency of the product desired. For example, a pin mill will yield a product having a flour-like consistency, while the disk mill or the hammer mill will yield a product with a granular consistency.

The above process yields a natural source of tryptophan having a tryptophan content that is greater than its parent source. Preferably, the material should provide at least 0.2% by weight tryptophan. The resultant, at least partially, defatted seed meal can then be incorporated into compositions useful for inducing sleep.

In addition to the partially defatted meal, the composition should contain a carbohydrate source with a high glycemic index, preferably in the form of glucose, although sucrose and other sugars that breakdown into glucose can be used. Without wishing, to be bound by theory, it is believed that the carbohydrate source facilitates the uptake of tryptophan across the blood brain barrier where it can be made available for metabolism into serotonin. In the human a barrier exists that allows the brain functions to operate in an independent environment from the rest of the body which protects the sensitive nature of the CNS. This barrier is the result of countless tight junctions between the cerebral endothelial cells at the blood-brain interface that restricts diffusion into the brain (Saunders et al., 1991). Superimposed on the diffusion provided by the tight junctions is a series of transport mechanisms into and out of the brain that regulate the internal environment of the brain with respect to a wide range of molecules including electrolytes, glucose, vitamins and amino acids. The transport mechanism for tryptophan is utilized by other large neutral amino acids (LNAA) as well (Lajtha, 1974; Betz and Goldstein, 1978). Competition for these transport sites is the reason that a large high protein meal fails to induce a hypnotic effect despite containing sufficient tryptophan (Moller, 1983). Conversely, in the same study, high carbohydrate meals with relatively small amounts of tryptophan did induce a mild hypnotic effect. This apparent contradiction is explained by the shunting of competing LNAA to liver and muscle tissue at times of relatively high insulin serum levels (Fernstrom and Wurtinan, 1971). Tryptophan is not shunted in this manner and consequently, any free tryptophan is afforded an insulin-induced competitive advantage of the transport sites across the BBB.

The carbohydrate source should be present in an amount sufficient to induce an increase in blood insulin levels in the individual consuming the composition. The tryptophan/LNAA ratio increases with increased insulin levels. An increase from 15 microunits/ml to 60 microunits/ml results in an approximately 35% increase in the tryptophan/LNAA ratio. This level of increase is sufficient although less significant increases will also be beneficial. Preferably, the amount of glucose present in the composition is from about 25 g to about 150 g, with 75 g being most preferred. The amount of tryptophan will remain constant but increases in the carbohydrate will increase the tryptophan/LNAA ratio. Other carbohydrate sources may include maltose, sucrose, etc., but not fructose given its low glycemic index. For individuals that are obese or have type II diabetes, a higher amount of carbohydrate (e.g., 100 g) may be required because of abnormal insulin responses to glucose.

Most (approximately 80%) of tryptophan is protein bound. It is only a small pool of free tryptophan that actually competes with other LNAAs for entry into the brain. Consequently, under ordinary conditions tryptophan that is ingested, is quickly stored in the "albumin reservoir" and has little impact on the availability of CNS tryptophan unless given in superphysiological amounts. If, however, tryptophan becomes available at a time when insulin levels increase, free fatty acids compete for the "albumin reservoir" thereby shifting existing protein-bound to free tryptophan, as well as preventing the incorporation of the newly ingested tryptophan. Thus, whilst the serum levels of competing LNAAs are reduced, two separate sources of tryptophan (existing protein-bound and new ingested tryptophan) result in increased free tryptophan. In view of this, it may be desirable to produce a product that contains at least some residual oil content to preserve a portion of the fatty acids present in the plant material or seed. For squash seeds, about 20% residual oil remaining in the seed meal is optimal. For other seeds, it may be necessary to add other fatty acids back into the partially defatted product to provide the optimal balance of fatty acids. Hydrogenated oils or other oils can be added for this purpose, such as canola oil, sunflower oil, safflower oil, palm kernel oil, corn oil or milk solids.

In a preferred embodiment, the composition comprises at least partially defatted squash seeds, particularly butternut squash seeds, pumpkin seeds, peppercorn seeds and combinations thereof, glucose in an amount sufficient to facilitate uptake of the tryptophan contained in the squash seeds across the blood brain barrier in the individual consuming the composition, and vitamins B3 and B6 in amounts present to facilitate tryptophan uptake.

In another embodiment, the composition will comprise at least partially defatted butternut squash seed meal (e.g., from about 50 g to about 100 g) in an amount sufficient to provide about 250 mg to about 1000 mg tryptophan, and from about 25 g to about 200 g glucose. More particularly preferred is a composition comprising from about 25 g to about 50 g defatted butternut squash seed meal (pressed to reduce the oil content by 75%) and from about 75 g to about 100 g glucose. Optionally, the composition will comprise vitamin B3 and/or vitamin B6. Vitamin B3 can be added in amounts of from about 5 mg to about 50 mg; and vitamin B6 can be added in amounts of from about 0.5 mg to about 50 mg, with 50 mg of each of vitamins B3 and B6 being preferred.

The composition and dietary supplements of the invention are intended to be orally administered daily. How the compositions are formulated will depend upon intended use. For example, for sleep augmentation, the compositions may be formulated for single daily administration prior to bedtime. Alternatively, the compositions may be formulated in multiple portions or as time release compositions for more or less frequent administration; for example, the dietary supplement may be formulated as two tablets for twice daily administration, particularly for disorders associated with low seratonin levels. For reasons of size (ease of swallowing) or improved bioabsorption or utilization (e.g., before or after a meal or before sleep), a given dosage may be divided into two, three, or more tablets (or capsules, etc.). A daily dosage may be administered as one tablet, as two tablets taken together, or as two tablets taken separately (e.g., one in the morning and one in the evening). The recommended daily amounts of each ingredient, as described above, serve as a guideline for formulating the dietary supplements of this invention. The actual amount of each ingredient per unit dosage will depend upon the number of units daily administered to the individual in need thereof. This is a matter of product design and is well within the skill of the dietary supplement formulator.

The dietary supplements of the present invention may be formulated using any pharmaceutically acceptable forms of the vitamins, minerals and other nutrients discussed above, including their salts. They may be formulated into capsules, tablets, powders, suspensions, gels or liquids optionally comprising a physiologically acceptable carrier, such as but not limited to water, milk, juice, starch, vegetable oils, salt solutions, hydroxymethyl cellulose, carbohydrate. The dietary supplements may be formulated as powders, for example, for mixing with consumable liquids, such as milk, juice, water or consumable gels or syrups for mixing into other dietary liquids or foods. The dietary supplements of this invention may be formulated with other foods or liquids to provide premeasured supplemental foods, such as single servings bars, for example.

The dietary supplement can be made in a variety of forms, such as baked goods, (e.g., cookies, brownies, fudge, cake, breads, biscuits, crackers,), puddings, confections, (i.e., candy), snack foods (e.g., pretzels, chips), dietary beverages, ice cream, frozen confections and novelties, or non-baked, extruded food products such as bars. The preferred form is a non-baked extruded nutritional bar.

The dietary supplement can also contain other ingredients such as one or a combination of other vitamins, minerals, antioxidants, fiber and other dietary supplements. Selection of one or several of these ingredients is a matter of formulation design, consumer and end-user preference. The amount of these ingredients added to the dietary supplements of this invention are readily known to the skilled artisan and guidance to such amounts can be provided by the U.S. RDA doses for children and adults. Vitamins and minerals that can be added include, but are not limited to, calcium phosphate or acetate, tribasic; potassium phosphate, dibasic; magnesium sulfate or oxide; salt (sodium chloride); potassium chloride or acetate; ascorbic acid; ferric orthophosphate; niacin amide; zinc sulfate or oxide; calcium pantothenate; copper gluconate; riboflavin; beta-carotene; pyridoxine hydrochloride; thiamin mononitrate; folic acid; biotin; chromium chloride or picolonate; potassium iodide; sodium selenate; sodium molybdate; phylloquinone; Vitamin $D_3$; cyanocobalamin; sodium selenite; copper sulfate; Vitamin A; Vitamin E; vitamin $B_6$ and hydrochloride thereof; Vitamin C; inositol; Vitamin $B_{12}$; potassium iodide.

The dietary supplement can comprise one or a combination of antioxidants in therapeutic amounts. Antioxidants suitable for use in this invention include but are not limited to, vitamin, A, vitamin C, vitamin E, β-carotene, zinc, chromium, selenium and herbs, such as ginkgo biloba, ginseng. The amount of antioxidant(s) per unit serving are a matter of design and will depend upon the total number of unit servings of the dietary supplement daily administered to the patient. The total amount of antioxidant(s) will also depend, in part, upon the condition of the patient. Preferably the amount of antioxidant(s) will be a fraction or multiplier of the RDA amounts. For example, the dietary supplement will comprise 50% RDA antioxidants per unit dosage and the patient will consume two units per day.

Flavors, coloring agents, spices, nuts and the like can be incorporated into the product. Flavorings can be in the form of flavored extracts, volatile oils, chocolate flavorings, peanut butter flavoring, cookie crumbs, crisp rice, vanilla or any commercially available flavoring. Examples of useful flavorings include but are not limited to pure anise extract, imitation banana extract, imitation cherry extract, chocolate extract, pure lemon extract, pure orange extract, pure peppermint extract, imitation pineapple extract, imitation rum extract, imitation strawberry extract, or pure vanilla extract; or volatile oils, such as balm oil, bay oil, bergamot oil, cedarwood oil, cherry oil, walnut oil, cinnamon oil, clove oil, or peppermint oil; peanut butter, chocolate flavoring, vanilla cookie crumb, butterscotch or toffee. In a preferred embodiment, the dietary supplement contains non-caffeinated cocoa or chocolate, or chocolate substitutes, such as carob. The food compositions may further be coated, for example with a yogurt coating.

Emulsifiers may be added for stability of the final product. Examples of suitable emulsifiers include, but are not limited to, lecithin (e.g., from egg or soy), and/or mono- and di-glycerides. Other emulsifiers are readily apparent to the skilled artisan and selection of suitable emulsifier(s) will depend, in part, upon the formulation and final product.

Preservatives may also be added to the dietary supplement to extend product shelf life. Preferably, preservatives such as potassium sorbate, sodium sorbate, potassium benzoate, sodium benzoate or calcium disodium EDTA are used.

In addition to the carbohydrates described above, the dietary supplement can contain artificial sweeteners, e.g., saccharides, cyclamates, aspartamine, aspartame, acesulfame K, and/or sorbitol. Such artificial sweeteners can be desirable if the dietary supplement is intended for an overweight or obese individual, or an individual with type II diabetes who is prone to hyperglycemia.

To manufacture such a food bar, the liquid ingredients are cooked; the dry ingredients are added with the liquid ingredients in a mixer and mixed until the dough phase is reached; the dough is put into an extruder, and extruded; the extruded dough is cut into appropriate lengths; and the product is cooled. For manufacture of other foods or beverages, the ingredients comprising the dietary supplement of this invention can be added to traditional formulations or they can be used to replace traditional ingredients. Those skilled in food formulating will be able to design appropriate foods/beverages with the objective of this invention in mind.

The invention can be used to induce sleep in individuals in need thereof. Patients suffering from insomnia, such as caused by stress or side effects of medication can benefit from the compositions described herein. Further, the compositions can be used as an adjunct in the treatment of psychiatric disorders by providing a tryptophan source that can be transported to the brain and metabolized into serotonin. Thus, the compositions can be used to ameliorate the effects of reduced serotonin levels in an individual which manifest as depression, anxiety disorders, obsessive compulsive disorders, pain disorders, aggression and eating disorders. The daily recommended amount of tryptophan would depend in part on the medical reason for tryptophan supplementation, the age and condition of the individual and medication(s) the individual is/are taking. The practitioner would be able to evaluate these factors and determine the proper recommended dosage.

The hypnotic effects of tryptophan are well studied and follow a fairly flat dose-response curve (for review see Schneider-Helmut and Spinweber, 1986). When given alone, 1 gm of tryptophan is sufficient to produce improved sleep in the majority of people with mild insomnia. Higher dosages (2–12 gm) offer little extra benefit and indeed at the highest dosages (12 gm) sleep was disrupted despite a reduction in sleep latency (Griffiths et al., 1972). Later studies show that dosages greater than 1 gm do not significantly shorten the sleep latency but are associated with a subjective experience of drowsiness (George et al., 1989). Wyatt and colleagues (1970) were the first to describe that ongoing use of tryptophan leads to an increase in Total Sleep Time (TST) which persists for days after the tryptophan treatment is discontinued. In psychiatric conditions as little as 250 mg of tryptophan per day can aid in increasing the concentration of serotonin offering significant clinical improvement.

It is noted that there are potential side effects with tryptophan supplementation. Tryptophan at lower dosages have few side effects but there are reports of difficulties at higher dosages or in combination with certain antidepressants. When combined with a monoamine oxidase inhibitor (MAOI), tryptophan carries a risk of delirium and neurological dysfunction (Thomas and Rubin, 1984). At higher dosages (greater than 12 gm per day) the most frequent complaints are daytime sedation and nausea (Hartmann, 1977). There are a few theoretical risks that have been demonstrated in animal models but not in humans. Large dosages of 1-tryptophan produce lipogenesis in animals (Fears and Murrell, 1980) but this effect was not seen in humans (Sourkes, 1983). Similarly there is a theoretical risk that a tryptophan metabolite, xanthurenic acid may lead to the development of diabetes (Kotake and Murakami, 1971). Thus, it is an objective of the present invention to limit the daily amount of tryptophan administered to an individual to levels below about 12 g per day to avoid these potential side effects.

The invention will be further illustrated by the following examples which are not intended to be limiting in any way. All references cited herein are incorporated in their entirety.

EXAMPLES

Example 1

Procedure for Defatting Seeds Using a Modified Oil Press

Flaking

Initial flaking of the squash seeds is done to rupture oil cells and to prepare a thin flake with a large surface area for pre-pressing by passing seeds through a set of smooth rollers using a lab scale flaking mill.

Conditioning

Conditioning is done to further rupture oil cells, increase pliability of the flakes and increase the efficiency of the expeller by lowering the viscosity of the oil contained. The conditioning of the flaked seeds was undertaken in a microwave for from about 1 minute to about 2 minutes to achieve a temperature between 40–45° C.

Pressing

The heated seeds are then pressed using a mechanical press (Gusta Laboratory Press set to 4.5 amps) to remove approximately ⅔ oil with 22% by weight residual oil content in the press cake.

Example 2

Tryptophan Analysis of the Defatted Seed Meal

A. High Pressure Liquid Chromatography (HPLC)

With pure protein or peptides, amino acid determination is relatively easily made with High Pressure Liquid Chromatography (HPLC). HPLC requires the hydrolysis of protein into the constituent amino acids that are then run in a column under pressure. The column causes the various amino acids to run at different speeds dependent on the size and charge. The determination of a tryptophan within a food source is, however, more complicated because of its ability, especially in the peptide form, in the presence of light, heat, hydrogen and hydroxyl ions (Concon, 1975). This difficulty may explain, in part, the problems in quantifying tryptophan within food in a reliable fashion utilizing HPLC with possible tryptophan losses of 10–30% (Landry and Delhaye, 1996). Relying on the presence of an aromatic ring within the tryptophan molecule, a spectrophotometric method was utilized at the Guelph Food Technology Centre that allowed for the reliable quantification of tryptophan (Balestrierl et al., 1978).

B. Second Derivative Spectroscopy

The quantitative determination of aromatic amino acids in proteins is possible with second derivative spectroscopy, an analysis of the ultraviolet absorption spectra within a certain wavelength. Derivative spectroscopy is superior to direct spectroscopy through the elimination of spectral interference. In the case of tryptophan, direct spectroscopy produces a sloping background absorbence. Second derivative spectroscopy eliminates any background absorbence allowing the tryptophan absorbence to be quantified at a wavelength of approximately 280 nm.

Example 3

Comparitive Analysis of Defatted Pumpkin, Butternut and Peppercorn Squash Seeds Pumpkin seeds, butternut squash seeds and peppercorn squash seeds were flaked, conditioned and pressed according to the procedure set forth in Example 1. Using second derivative spectroscopy, the tryptophan content of the seed meal was determined and the results set forth in the Table below. Screening of butternut squash, peppercorn squash and pumpkin seeds revealed that all have high tryptophan contents but that butternut squash seeds are highest in tryptophan. It also revealed that 100 gm of defatted butternut squash seed meat contains in excess of 1000 mg of tryptophan. For butternut squash, the ratio of seeds to the final seed meal is approximately one third.

TABLE

| Source | Tryp/Total Protein (mg/g) | Tryp/defatted meal protein, starch, fiber) (mg/g) | Oil (g/kg) | Crude Protein (g/kg) (intact seed) |
| --- | --- | --- | --- | --- |
| Pumpkin seed defatted meal | 17.9 | 7.35 | 333 | 208 |
| Butternut squash seed defatted meal | 23.8 | 10.1 | 403 | 221 |
| Pepper squash seed meal | 17.9 | 8.14 | 446 | 202 |

HPLC analysis on partially dehulled and partially defatted butternut squash seeds are as follows:
Valine - 1.445%
Isoleucine - 1.115%
Leucine - 2.111%
Tyrosine - 1.316%
Phenylalanine - 1.481%

REFERENCES

Betz A. L. and Goldstein, G. W., Science, 202:225–227 (1978).

Boman, B., Aust. NZ J. Psychiatry, 22:83–97 (1988).

Balestriel, C., et al., European Journal of Biochemistry, 90:433–440 (1978).

Fears, R., and Murrell, F. A., British Journal of Nutrition, 43:349–356 (1980).

Fermstrom, J. D. and Wurtrnan, R. J, Science, 174:1023–1025 (1971).

George, C. F., et al., Sleep, 12:345–53 (1989).

Griffiths, W. L., et al., Psychobiology, 9:345–356 (1972).

Hartmann, E., American Journal of Psychiatry, 134:366–370 (1977).

Kotake, Y. and Murakami, E., *American Journal of Nutrition American Journal of Clinical Nutrition*, 24:826–829 (1971).

Lajtha, A., In *Aromatic Amino Acids in the Brain* (CIBA Foundation Symposium 22)

New York: American Elsevier pp. 25–49 (1974).

Moller, S. E., *Human Neurobiology*, 2:41–8 (1983).

Sourkes, T. L., *Advances in Biological Psychiatry*, 10:160–173 (1983).

Schneider-Helmet, D. and Spinweber, C. L., *Psychopharmacology*, 89:1–7 (1986).

Saunders, N. R., et al., *Clinical and Experimental Pharmacology and Physiology*, 26:11–19 (1999).

Thomas, J. M. and Rubin, E. H., *American Journal of Psychiatry*, 141:281–283 (1977).

Wyatt, R. J. et al., *Lancet II*, 84:842–846 (1970).

While this invention has been particularly shown and described with references to preferred embodiments thereof, it will be understood by those skilled in the art that various changes in form and details may be made therein without departing from the scope of the invention encompassed by the appended claims.

What is claimed is:

1. A composition comprising partially defatted meal from a plant source naturally containing tryptophan, an added carbohydrate source having a high glycemic index present in the composition in an amount sufficient to facilitate transport of tryptophan across the blood brain barrier in an individual, and optionally a physiologically acceptable vehicle; wherein the plant source has been processed to partially remove oil contained therein to yield a natural source of tryptophan greater than its parent plant source, said plant source being butternut squash seed such that said meal provides from about 25 mg to 1000 mg tryptophan.

2. The composition of claim 1 that is in the form of a tablet, powder, suspension, liquid, capsule or gel form.

3. A dietary supplement comprising the composition of claim 1.

4. A dietary supplement of claim 3 wherein the supplement is formulated into a plurality of oral dosage forms for ingestion on a daily basis.

5. The dietary supplement of claim 3 wherein the supplement is provided as a dietary bar.

6. A composition according to claim 1 comprising at least partially defatted butternut squash seed meal providing from about 250 mg to about 1000 mg tryptophan and from about 25 mg to about 200 mg of glucose and optionally a physiologically acceptable vehicle.

7. A composition according to claim 1 comprising at least partially defatted butternut squash seed meal providing from about 25 mg to about 50 mg tryptophan and from about 75 mg to about 100 mg of glucose and optionally a physiologically acceptable vehicle.

8. The composition of claim 6 further comprising from about 5 mg to about 50 mg vitamin B3; from about 0.5 mg to about 50 mg vitamin B6, and combinations thereof.

9. A food or beverage comprising the composition of claim 1.

10. The food or beverage of claim 9 wherein the food is a cookie, food bar, baked good, snack food or candy bar.

11. A dietary supplement of claim 3 wherein the supplement is in the form of a powder.

12. The composition of claim 1 wherein the added carbohydrate source is selected from the group consisting of glucose, maltose, sucrose and combinations thereof.

13. The composition of claim 1 further comprising vitamin B3 and/or B6 in an amount sufficient to facilitate uptake of the tryptophan.

14. A food or beverage comprising the composition of claim 1, wherein the amount of carbohydrate present in the composition is from about 25 g to about 200 g together with 50 g to 100 g of defatted butternut squash meal providing 250 mg to 1000 mg tryptophan.

* * * * *